US009149179B2

(12) United States Patent  
Barnard et al.

(10) Patent No.: US 9,149,179 B2
(45) Date of Patent: Oct. 6, 2015

(54) SYSTEM AND METHOD FOR IDENTIFYING EYE CONDITIONS

(71) Applicant: IRISS Medical Technologies Limited, London (GB)

(72) Inventors: Nigel Andrew Simon Barnard, London (GB); Ron Uriel Maor, London (GB); Yuval Yashiv, London (GB)

(73) Assignee: IRISS MEDICAL TECHNOLOGIES LIMITED, London (GB)

( * ) Notice: Subject to any disclaimer, the term of this patent is extended or adjusted under 35 U.S.C. 154(b) by 0 days.

(21) Appl. No.: 14/351,241

(22) PCT Filed: Oct. 24, 2012

(86) PCT No.: PCT/GB2012/052631
§ 371 (c)(1),
(2) Date: Apr. 11, 2014

(87) PCT Pub. No.: WO2013/061050
PCT Pub. Date: May 2, 2013

(65) Prior Publication Data
US 2014/0285768 A1 Sep. 25, 2014

(30) Foreign Application Priority Data

Oct. 24, 2011 (GB) .................................. 1209325.8
Oct. 24, 2011 (IL) ......................................... 215883

(51) Int. Cl.
A61B 3/14 (2006.01)
A61B 3/10 (2006.01)
(Continued)

(52) U.S. Cl.
CPC ............ *A61B 3/0025* (2013.01); *G06K 9/0061* (2013.01); *G06T 7/0014* (2013.01); *G06T 2207/30041* (2013.01)

(58) Field of Classification Search
USPC ......... 351/200, 205, 206, 208–211, 221, 222, 351/246–245; 382/117, 103, 194, 190, 191, 382/195, 305
See application file for complete search history.

(56) References Cited

U.S. PATENT DOCUMENTS 5,989,194 A 11/1999 Davenport et al.
6,089,715 A 7/2000 Hoover et al.
(Continued)

FOREIGN PATENT DOCUMENTS

EP 1 602 321 A1 12/2005
WO WO 03/030073 A1 4/2003

OTHER PUBLICATIONS

Intellectual Property Office of the United Kingdom, Certificate of Grant of Patent, GB2491941, United Kingdom Application No. GB1209325.8, Sep. 25, 2013, 1 Page.
(Continued)

Primary Examiner — Joseph P Martinez
Assistant Examiner — Brandi Thomas

(57) ABSTRACT

An electronic device comprising a processor utility configured and operable for processing image data, determining whether an abnormality exists in an image of a subject's eye, and generating corresponding output data, said processor utility comprising: a first processor configured and operable for selecting in the image data an image comprising a region of interest including predetermined eye features of at least one of two eyes of the subject, the first processor further configured and operable for pre-processing the image to determine whether it is suitable for image processing and for providing an indication of the determined suitability of the image; an eye feature detection utility configured and operable for applying an image processing algorithm to a suitable image for determining one or more parameters of the eye features from a set of predetermined parameters; and an eye condition identifier utility configured and operable for processing and analyzing said one or more parameters and generating data indicative of whether an abnormality exists in the image.

20 Claims, 7 Drawing Sheets

(51) Int. Cl.
*A61B 3/00* (2006.01)
*G06T 7/00* (2006.01)
*G06K 9/00* (2006.01)

(56) References Cited

U.S. PATENT DOCUMENTS 6,523,954 B1    2/2003   Kennedy et al.
7,854,509 B2 *  12/2010  Johns .................... 351/206

OTHER PUBLICATIONS

Intellectual Property Office of the United Kingdom, Examination Report Under Section 18(3), United Kingdom Application No. GB1209325.8, May 24, 2013, 2 Pages.

Intellectual Property Office of the United Kingdom, Examination Report Under Section 18(3), United Kingdom Application No. GB1209325.8, Dec. 24, 2012, 3 Pages.

Intellectual Property Office of the United Kingdom, Search Report Under Section 17(5), United Kingdom Application No. GB1209325.8, Sep. 21, 2012, 4 Pages.

Marks&Clerk LLP, Response to Examination Report Under Section 18(3), United Kingdom Application No. GB1209325.8, Feb. 7, 2013, 21 Pages.

Marks&Clerk LLP, Response to Examination Report Under Section 18(3), United Kingdom Application No. GB1209325.8, Jul. 24, 2013, 33 Pages.

Patent Cooperation Treaty, International Search Report and Written Opinion, International Patent Application No. PCT/GB2012/052631, Mar. 11, 2013, 14 Pages.

* cited by examiner

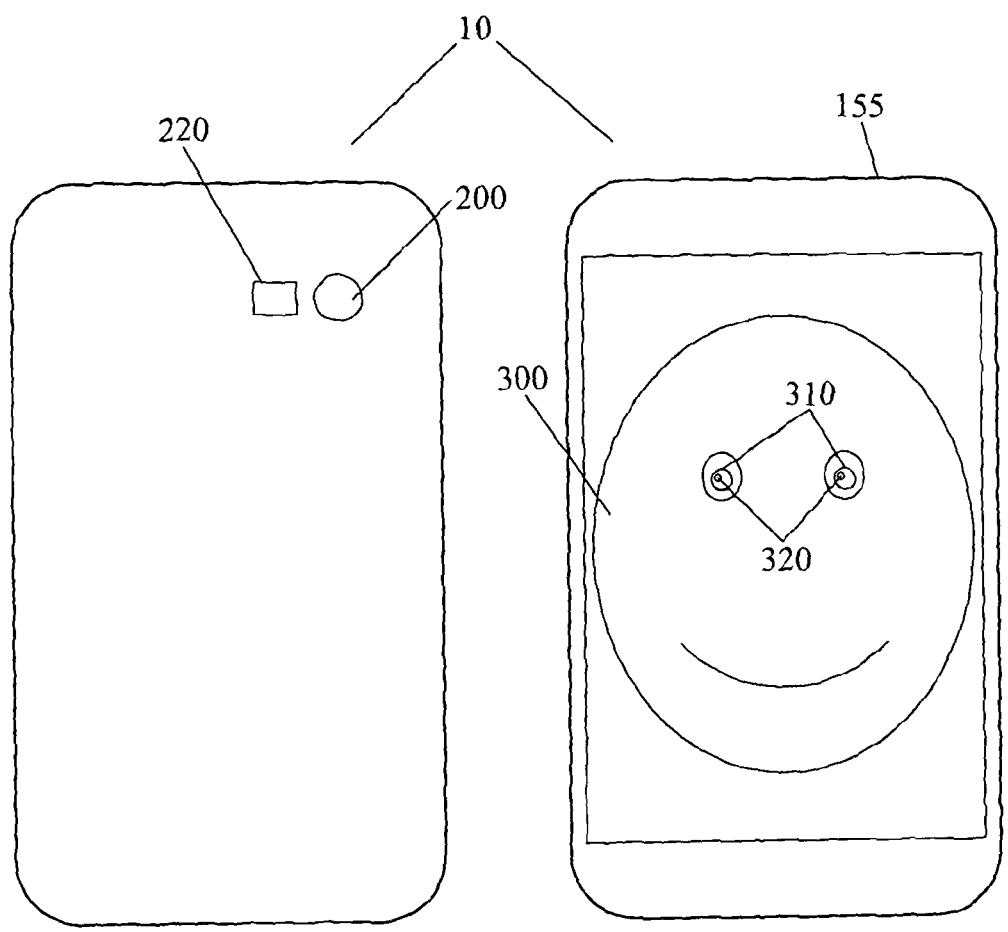
Fig. 3A                    Fig. 3B

SYSTEM AND METHOD FOR IDENTIFYING EYE CONDITIONS

RELATED APPLICATIONS

This application is the U.S. national phase of PCT/GB2012/052631 and claims foreign priority to United Kingdom application number GB1209325.8 filed Oct. 24, 2011, and Israel application number 215883 filed Oct. 24, 2011, which are hereby incorporated by reference in their entirety.

FIELD OF THE INVENTION

This invention is generally in the field of medical devices, and relates to a device and method for identifying abnormalities in the subject's eyes, such as strabismus.

BACKGROUND OF THE INVENTION

Strabismus is the misalignment of the visual axis between the two eyes, and is the chief cause of amblyopia—reduced visual acuity in one eye which cannot be improved by glasses. Amblyopia is responsible for loss of vision in one eye in children and young adults more than all other causes combined in the Western world. It was found that 2%-4% of children develop strabismus at an early stage. Therefore, early detection of strabismus and amblyopia is essential if it is to be treated effectively. The efficiency of known treatment techniques reduces with age up until 7 or 8 years, after which the loss of vision is permanent. Numerous medical bodies around the world, such as the American Academy of Paediatricians, recommend vision screening no later than the age of 4, if not earlier. Nevertheless, children younger than 5 are difficult to screen, and less than 1 in 3 from this age group in the US undergo vision tests. Also, there are various other conditions which may cause amblyopia, such conditions include anisometropia which is a difference in refractive power between the two eye lenses, and opacities being a condition of cataract.

The conventional tests for strabismus detection and diagnosis are typically manual tests, and have to be performed by professionals. These manual tests include the Hirschberg Test and the Cover Test and are best performed by ophthalmologists and orthoptists. The Hirschberg test involves shining a light into patient's eyes and visually inspecting the eyes for symmetry in the reflection of light (the Purkinje image) from the corneal surface. The Cover Test involves covering one eye at a time and observing eye movement while the patient fixates on a specific target. Strabismus and other conditions may also be inspected via the Bruckner Test, which is also a manual (visual) test. These tests are difficult to perform on non-cooperating patients, such as infants and young children. Front line medical staff, such as general practitioners and paediatricians, typically screen patients for strabismus, but as they are not skilled experts for these manual tests, this leads to both under-referrals and over-referrals.

Attempts have been made to develop techniques facilitating determination of various eye diseases/abnormalities. For example, U.S. Pat. No. 7,854,509 describes an article and method for screening vision that does not require verbal input from a test person or the test person to maintain a fixed position during the screening. The article includes an image capture device, at least one test light, a processing unit that includes an interpretive program, and a display. The method comprises capturing an image of a person's eyes, verifying the image, studying the image, evaluating the image, and displaying the results. Conveniently, the article and method require no special training by an operator.

General Description

There is a need in the art for a novel technique for simple, automatic detection of various eye conditions, such as strabismus, anisometropia, anisocoria, as well as retinoblastoma and cataract.

The present invention provides a device according to claim 1. Further optional embodiments and aspects of the invention are described in claim 2 et seq.

In accordance with one aspect of the invention there is provided an apparatus and method for fully automatic detection of eye conditions associated with abnormalities in a subject's eyes. The technique can be used for identifying eye conditions in children or infants or other subjects which may be less cooperative using an inspection procedure. The inspection procedure may be simple and quick and does not require a skilled professional operator. Moreover, the inspection may utilize data indicative of a single image of the subject's eyes, where the image may be acquired by a digital camera typically installed in most portable electronic devices, such as mobile phone devices, smartphones, as well as portable computer, PDA, etc. Also, a device of the present invention may be installed in a digital camera or ophthalmoscope, specifically designed for implementing the invention.

The conventional tests for diagnosing strabismus, e.g. the Hirschberg test, are manual tests which require a skilled professional and are limited to detection of medium to large amplitude strabismus. When testing for eye conditions in children/infants, who are typically less cooperative, the test is even less accurate or reliable. An automatic (computerized) system for identifying eye conditions can provide more accurate diagnostics, and can provide at least preliminary results in a very short time, while requiring less patient cooperation.

The present invention provides for a novel approach for processing and analyzing image data, which enables the technique or processor utility of the present invention to be embedded in any electronic device, being a personal computer, laptop, or any hand held computing device such as a smartphone, tablet, digital camera, or ophthalmoscope. The electronic device may utilize a camera unit installed therein to acquire one or more images of a region of interest and provide image data, or it may be connectable (via wires or wireless signal transmission) to an external camera unit or storage device to receive image data therefrom, thus operating in either on-line (real time) or off-line inspection mode. The electronic device configured for carrying out the present invention thus comprises a processor utility which is configured as a software application preprogrammed to receive and analyze image data, and may also include or be connectable to an output utility (e.g. screen) for providing analysis results and other instructions to an operator.

In the non limiting examples described below, the device of the invention is referred to as a computing device which includes a camera unit integral with the device. It should, however, be understood that the present invention is not limited to such an integral device configuration, and may be implemented as a chip or software/hardware utility that may be embedded in any electronic or computing device for receiving and processing image data including but not limited to cameras, smartphones, mobile phones, ophthalmoscopes.

In the simplest example, where the electronic device of the invention is integral with a camera unit (e.g., a hand held computing device including a camera unit), a user operates the camera unit to acquire one or more images of a subject's face utilizing flash light or other light source. Image data is received by the processor utility which is preprogrammed according to the invention for analyzing this data, identifying abnormal eye conditions of the subject, and generating output data indicative thereof. To this end, the processor utility performs a so-called pre-processing to identify existence and location of a region of interest (i.e. the left and/or right eye region(s) of a subject) within the image in order to determine whether said image is a proper one to be used for further processing or another image is needed. The proper zone/region is that including desired eye features for detection of one or more abnormalities in the subject's eye(s). Such eye regions may for example include a pupil and a bright zone associated with reflection of a light source (light reflection from the eye surface is commonly known as a Purkinje image) for at least one of the left and right eyes of a subject.

According to one broad aspect of the invention, there is provided a portable electronic device comprising a processor utility configured and operable for processing image data, determining one or more conditions indicative of an abnormality in a subject's eye, and generating corresponding output data, said processor utility comprising: a first processor configured and operable for selecting in the image data an image comprising a region of interest including predetermined eye features of at least one of two eyes of the subject; an eye feature detection utility configured and operable for applying an image processing algorithm to the region of interest in the selected image for determining one or more parameters of the eye features from a set of predetermined parameters; and an eye condition identifier utility configured and operable for processing and analyzing said one or more parameters and generating data indicative of a condition of the subject's eyes.

The set of predetermined parameters of the eye features may include at least one of geometrical, positioning and color related parameters of the eye features. Such parameter(s) of the eye features may comprise one or more of the following: location of the pupil for at least one of the eyes; location of the Purkinje image for at least one of the eyes; physical dimension of at least one of the pupils; physical dimension of at least one Purkinje image, average color of the pupils of both eyes, and average color of the Purkinje images of both eyes.

The region of interest is a part of the selected image including at least one of left and right eye regions, and preferably both of these eye regions. The region of interest in the selected image may also be that comprising at least one feature corresponding to predetermined imaging conditions. Such a feature corresponding to the predetermined imaging conditions may comprise a Purkinje image.

The device preferably comprises a memory utility for storing predetermined reference data. The latter includes first reference data indicative of pixel values corresponding to face features, and second reference data indicative of pixel values corresponding to eye features.

In some embodiments of the invention, the first processor module is configured and operable for carrying out the image selection by processing an image using the first reference data to obtain rough data about the region of interest in said image based on classifying pixels in the image according to the first reference data and grouping pixels into different categories relating to the region of interest.

In some embodiments of the invention, the eye feature detection module is configured and operable for processing the region of interest using the second reference data to obtain rough value of said one or more of the geometrical and/or positioning and/or color related parameters of the eye features by classifying pixels in the region of interest according to said second reference data and counting pixels relating to at least one eye feature. The eye feature detection module may use the rough values of one or more of such parameters for re-classifying the pixels related to said at least one feature, and weighting values of said re-classified pixels.

The eye features to be determined comprise at least one of pupil and Purkinje image in at least one of left and right eye regions. As indicated above, the parameters of the eye features may comprise location of the pupil for at least one of the eyes; location of the Purkinje image for at least one of the eyes; physical dimension of at least one of the pupils; physical dimension of at least one Purkinje image; and/or average color of the pupil and/or Purkinje images of one or both eyes.

In some embodiments of the invention, the eye condition identifier module is configured and operable to determine a relation between the parameters of at least two eye features, wherein said at least two eye features relate to the same eye region or to the different eyes' regions.

In some embodiments of the invention, the eye condition identifier module determines the relation between relative positions of the center of the Purkinje image and the center of the pupil in the right eye to those of the left eye, and identifies a deviation of said relation from a predetermined value. Such deviation is indicative of a degree of asymmetry corresponding to strabismus condition. The predetermined value may be a certain function of a difference between the relative positions in the left and right eye regions and a distance between the left and right pupils.

In some embodiments of the invention, the eye condition identifier module determines said relation in the form of a vector distance between the center of the pupil and the center of the Purkinje image in at least one of the left and right eye regions in the image, and identifies a deviation of said relation from a predetermined value. This deviation is indicative of strabismus condition of said at least one eye.

In some embodiments of the invention, the eye condition identifier module determines a relation between radii of the Purkinje image of the left and right eye regions, and identifies a deviation of said relation from a predetermined value being indicative of anisometropia condition.

In some embodiments of the invention, the eye condition identifier module determines a relation between average colors of pixels in the Purkinje image and/or pupil of the left and right eye regions, and identifies a deviation of said relation from a predetermined value. For example, such deviation from a predetermined value (threshold value) is indicative of anisometropia condition.

In some embodiments of the invention, the eye condition identifier module determines a relation between average colors of pixels in the pupil of the left and right eye regions, and identifies a deviation of said relation from a predetermined value being indicative of the presence of retinoblastoma or of a cataract in the eye.

In some embodiments of the invention, the eye condition identifier module is configured and operable to determine a relation between radii of pupils in the left and right eye regions, and to identify a deviation of said relation from a predetermined value being indicative of anisocoria condition.

The device of the present invention may be configured as or incorporated in a phone device (e.g. smartphone), a PDA device, a personal computer, a digital camera, tablet, laptop, or a specially designed ophthalmoscope.

The first processor module may be configured and operable for processing the image data and upon identifying image data pieces in the selected image corresponding to the subject's eyes, extracting said image data pieces to be processed by the eye feature detection module.

The processor utility may be configured and operable to operate the imager (internal or external) for generating the image data including a stream of images to be processed by the first processor module to select the proper image. In some embodiments, the processor utility selectively operates to generate a request data for additional image(s).

In a specific embodiment of the invention, the processing of the image data comprises the following: locating right and left eye regions in the selected image; locating a zone in the eye region corresponding to a Purkinje image, for right and left eyes of the subject; determining a dimension of the Purkinje image for the right and left eye regions; determining a relation between the dimension of said right and left Purkinje images, analyzing data indicative of said relation and generating data indicative of a anisometropia condition of the subject.

In a specific embodiment of the invention, the processing of the image data comprises the following: locating right and left eye regions in the selected image; locating zones corresponding to pupils of the right and left eye regions; locating a zone in the eye region corresponding to a Purkinje image, for right and left eyes of the subject; determining a relative location of the Purkinje image with respect to the pupil, for the right and left eye regions; and analyzing said relative location, and generating data indicative of a strabismus condition of the subject.

According to another broad aspect of the invention, there is provided a hand-held electronic device comprising: a frame grabber for acquiring images of the surroundings and generating image data including at least one image of at least one eye of a subject, a light source for illuminating said surroundings at least during a time of image acquisition, and a processor utility connected to said imager and configured and operable for processing said at least one image, determining one or more conditions indicative of an abnormality in the subject's eye(s), and generating corresponding output data. According to yet further aspect of the invention, there is provided a method for non-invasively screening subjects for certain one or more eye conditions using a hand-held device comprising a camera unit, a processor utility, a memory utility and a user interface utility. The method comprises:

a. operating the camera unit for providing image data indicative of one or more images taken by the camera unit at a certain distance from a subject, said distance ranging from a few centimeters to a few meters, b. processing said image data for validating presence therein of at least one image of one or both eyes of the subject;

c. processing said at least one image of one or both eyes of the subject and determining at least one of position, dimension and color related parameter of at least one eye feature including at least one of pupil and Purkinje images, and analyzing said at least one of the position, dimension and color parameters of at least one eye feature with respect to predetermined threshold data; and d. generating data indicative of existence or absence of one or more of the eye conditions.

According to yet another broad aspect of the invention, there is provided a control unit for embedding in an electronic device, said control unit comprising a connection utility for connecting to an imager, and a processor utility configured and operable for processing image data received from the imager and generating output data indicative of one or more abnormalities in a subject's eyes being imaged, said processing comprising determination of at least one of geometrical, positioning and color related parameters of eye features in at least one of right and left eyes of a subject.

According to yet further broad aspect of the invention, there is provided a computer program product embedded on a non-transitory computer-accessible medium and comprising a computer readable program code configured and operable for processing image data corresponding to subject's eyes and generating output data indicative of one or more abnormalities in the subject's eyes, said processing comprising determination of at least one of geometrical, positioning and color related parameters of eye features in at least one of right and left eyes of a subject.

The computer program product is capable selecting in the image data an image comprising a region of interest including predetermined eye features of at least one of two eyes of the subject; applying an image processing algorithm to the region of interest in the selected image for determining one or more parameters of the eye features from a set of predetermined parameters; and processing and analyzing said one or more parameters and generating data indicative of a condition of the subject's eyes. To this end, the computer program product accesses certain first and second reference data indicative of pixel values corresponding to respectively face features and eye features. Such reference data may be stored in an external storage utility to which the program has access or may actually be a part of the program itself. The program uses the first reference data for processing the image data to obtain rough data about the region of interest based on classifying pixels in the image according to said first reference data and grouping pixels of different categories relating to the region of interest, thereby selecting in the image data a proper image comprising a region of interest. Then, the second reference data is used for processing the selected proper image to obtain rough value of said at least one parameter of the eye features by classifying pixels in the region of interest according to said second reference data and counting pixels relating to at least one eye feature.

According to yet another aspect of the invention, there is provided an electronic device comprising a processor utility configured and operable for processing image data, determining one or more conditions indicative of an abnormality in a subject's eye, and generating corresponding output data, said processor utility comprising:

a first processor configured and operable for selecting in the image data an image comprising a region of interest including predetermined eye features of at least one of two eyes of the subject, said selecting comprising processing an image using a first reference data indicative of pixel values corresponding to face features to obtain rough data about the region of interest in said image based on classifying pixels in the image according to said first reference data and grouping pixels of different categories relating to the region of interest;

an eye feature detection utility configured and operable for applying an image processing algorithm to the region of interest in the selected image for determining one or more of geometrical and positioning parameters of the eye features, said applying of the image processing algorithm comprising using second reference data indicative of pixel values corresponding to eye features to obtain a value of said one or more of geometrical and positioning parameters of the eye features by classifying pixels in the region of interest according to said second reference data and counting pixels relating to at least one eye feature; and an eye condition identifier utility configured and operable for processing and analyzing said one or more geometrical and positioning parameters and generating data indicative of a condition of the subject's eyes.

BRIEF DESCRIPTION OF THE DRAWINGS

In order to understand the invention and to see how it may be carried out in practice, embodiments will now be described, by way of non-limiting examples only, with reference to the accompanying drawings, in which:

FIGS. 3A and 3B exemplify how the device of the present invention can be embedded in a phone device typically including a digital camera unit or a specially designed digital camera;

FIG. 5A illustrates a flow diagram of the image processing method and FIGS. 5B to 5F illustrate various features successively detected in the image being processed.

DETAILED DESCRIPTION OF EMBODIMENTS

As indicated above, identifying various eye conditions, especially in children or infants, is typically a complex task requiring highly skilled professionals. The currently used test of the kind specified, such as Hirschberg Test, can only find limited eye conditions and with limited accuracy. Additional tests, which include the Cover Test and the Bruckner Test, are considered the "gold standard" tests for some of these conditions, such as strabismus, but these require significant skill and experience, especially when performed on infants and very young children.

The present invention solves the above problems by providing a novel technique enabling simple and fully automatic identification of eye conditions associated with abnormalities of the eye, providing objective and referenceable test results. The technique of the present invention may be performed by a computing device, being hand-held or not, via a computer embedded software responsive to input image data.

Figure 1:
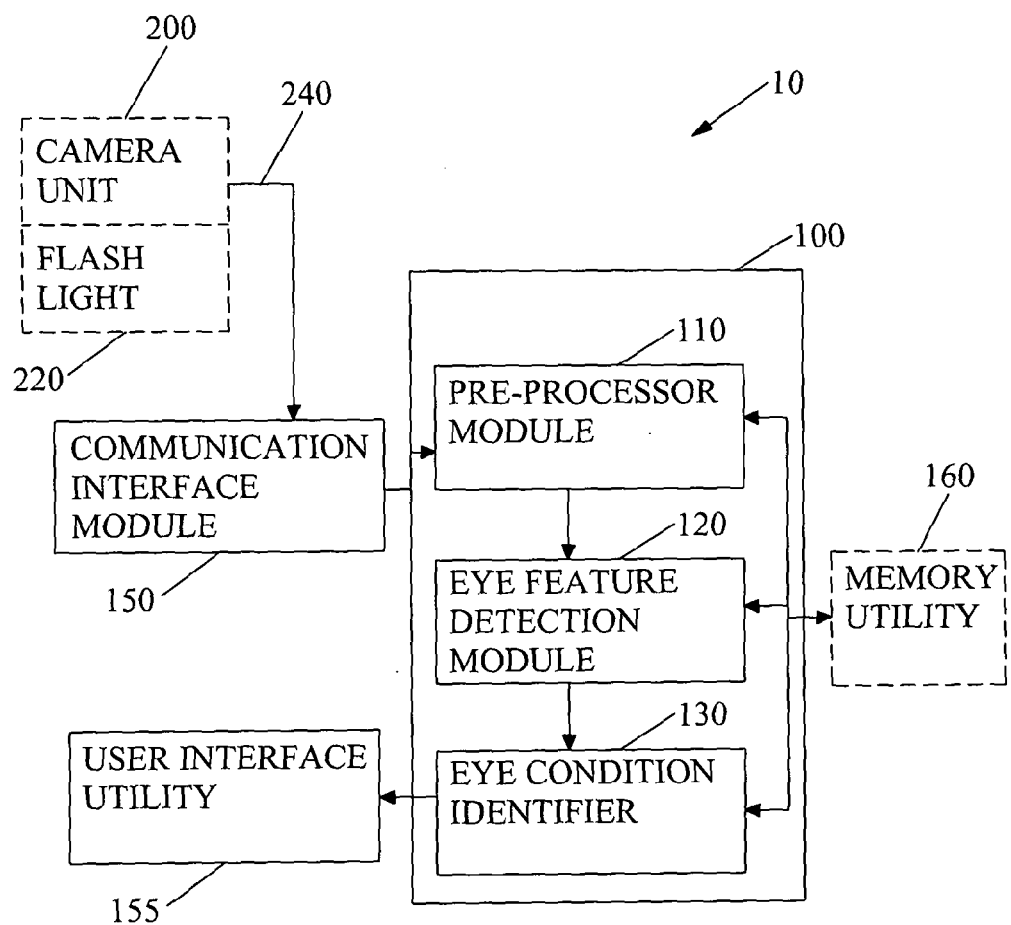
FIG. 1 is a block diagram of an example of an electronic device for detection of abnormal eye conditions according to the present invention.

FIG. 1 exemplifies, by way of a block diagram, a device 10 of the present invention configured and operable for detection of abnormal eye conditions. The device 10 is configured as a control unit (computing device) which includes a processor utility 100 configured to receive and process image data 240 applying thereto an image processing technique of the present invention. The image data includes at least one image of a subject's face which includes a region of interest. The latter includes predetermined eye features of at least one of the left and right eyes of a subject, for example left and right pupils, or a pupil and Purkinje images for at least one of the left and right eyes.

As exemplified in the figure, the device 10 may include an imager 200 as its constructional part or may be connectable to the external imager. It should be noted that the term "imager" used herein refers to either a camera unit itself or a storage device where image data from the camera unit is stored. The storage device may be either integral with a processor utility of the invention or a stand-alone device accessible by the processor utility. Although in the description below such imager is referred to as a camera unit, it should be understood that the principles of the invention are not limited to this specific example and the imager may be constituted by a storage device as well. In case an external imager is used, the image data 240 may be transmitted to the processor utility via a communication network.

The image data 240 includes a single image, or a series of still images of the subject. In some embodiments of the invention, the image data corresponds to predetermined imaging conditions, e.g. includes such eye-region features as a Purkinje image. To this end, image(s) is/are acquired while illuminating the subject's face with light from a point like light source 220, such as flash light. The flash light source 220 may be integral with the camera unit 200, or a separate unit. For the purposes of the present invention, image acquisition does not require the user/operator to be trained professional. What is needed in order to apply the image processing technique of the invention is a condition that the image includes a proper region of interest, i.e. a region including an image of at least one of the right and left eyes of a subject. For some applications, as will be described further below, the region of interest needs to include images of both the left and right eyes of a subject.

The processor utility 100 includes several processing modules configured and operable for performing different functions. A first processor module, a so-called pre-processor module 110, is configured and operable for receiving and processing image data and selecting an image comprising a region of interest, namely an image including predetermined eye features of at least one of two eyes of the subject. A second processor module is an eye feature detection module 120 which is configured for processing the region of interest in the selected image (i.e. applying an image processing algorithm thereto) for determining a set of predetermined parameters/conditions of the eye features including one or more of geometrical, positioning and color-related parameters of the eye features, e.g. the pupil of both eyes, or pupil and Purkinje image in at least one of the left and right eye regions. Another processor module is an eye condition identifier 130 configured and operable for processing and analyzing the geometrical and/or positioning and/or color parameters of the eye features and generating output data indicative of the eye's condition(s).

As shown in the figure, the device 10 may also include a communication module 150 for communication with external systems (e.g. via the network), a user interface utility 155, and a memory utility 160 for storing analysis results and/or image data to be processed, as well as certain reference data (look-up table parameters) used for pre-processing and eye feature detection. The device may also include a screen for displaying the image itself and possibly also providing visual presentation of the results. It should be understood that input data (reference data and/or image data) can be accessed via the device communication with an external storage system, as well as the analysis results can be transmitted to an external storage system.

The present invention provides for an image processing technique carried out by the eye feature detection module, and applicable to a single image captured by any known suitable camera unit. The present invention also provides for the effective pre-processing technique enabling correct image selection for the eye feature detection to be applied thereto. Both pre-processing (eye region(s) location in the image) and image processing (eye feature detection) are based on the use of certain reference data indicative of pixel values (intensities/colors) associated with different features within a region of interest, i.e. subject's face for the purposes of preprocessing and eye region(s) for the purposes of image processing, and further pixel classifying and counting within the respective regions. These techniques of the invention will be described in more details further below.

As indicated above, the technique of the present invention eliminates, or at least substantially reduces, the requirement for a trained professional in order to identify abnormal eye conditions. Reference is made to FIGS. 2, 3A-3B and 3C illustrating how the device of the present invention (processor utility) can be embedded in a laptop-like computer device associated with an external camera unit or in the camera unit itself (FIG. 2), or in a smart phone device typically including a built-in camera unit (FIGS. 3A-3B), or in an ophthalmoscope equipped with a camera unit. It should be noted that the operator (user) is required to operate the camera unit to solely take a simple and standard photograph, similar to everyday, amateur photography. It should be noted that these not limiting examples illustrate imager constituted by a camera unit, while it is mentioned above that imager, for the purposes of the present invention may also be a storage device.

Figure 2:
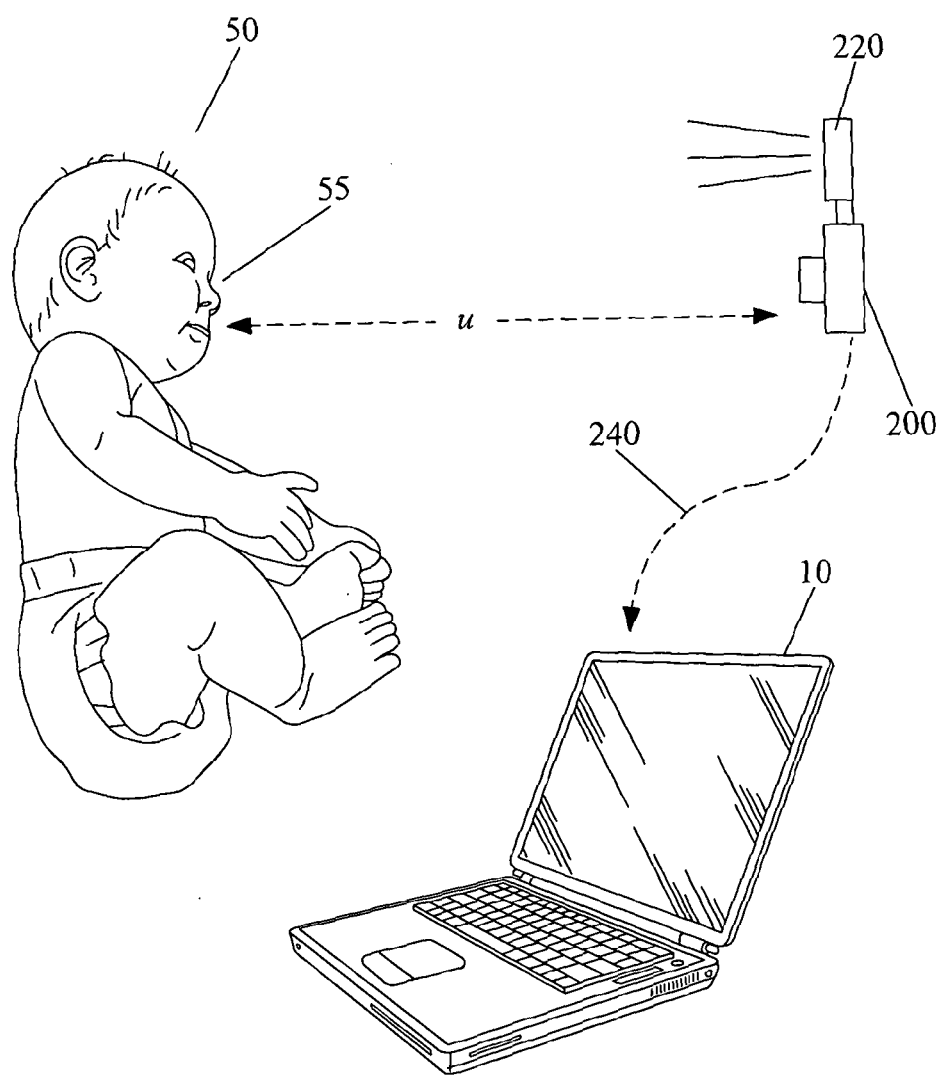
FIG. 2 illustrates how a handheld device of the present invention can be embedded in a laptop computer associated with a camera unit or embedded in the camera unit itself, and used for detection of abnormal eye conditions.

As shown in FIG. 2, in order to identify eye conditions of an infant 50, an operator, who may or may not be a trained professional, operates a camera unit 200 (which need not be a professional camera) in its "flash mode", i.e. utilizing flash light 220 to take one or more photographic images of the infant's face region 55, which are preferably centered and zoomed on the subject's face. To this end, images are acquired from an appropriate distance u determined according to parameters of the camera unit. The distance u can vary in accordance with the focal length of a lens used in the camera unit; for standard commercially available camera units the distance u is between 25 cm and 300 cm. It should be noted that for the operator's convenience, it is not a requirement for the distance to be a set distance, and a range of distances is perfectly acceptable. Images to be processed may be still images or a sequence of images forming a video stream. It should however be noted that for the purposes of the present invention, processing of a single image of the proper eye region(s) is sufficient, and practically an ability to obtain a series of images is preferred solely in order to select the image including proper presentation of a region of interest, namely a region including desired eye features.

The camera unit 200 includes a frame grabber (not shown) which acquires images of the surroundings and generates image data 240 indicative thereof which includes one or more images of the subject. This image data 240 may be stored in a memory card or any other memory utility within the camera unit or external to it, to be on-line (real time) or off-line (later) transmitted to the device 10. The camera unit may communicate with the computer device 10 via wired or wireless communication, or by transferring image data via SD card or the like. The processor utility of the invention installed in the computer device 10 receives and processes the image data for detection of abnormal eye conditions, and presenting the results on a computer display, in an appropriate format.

It should be understood that the device 10 of the invention may be embedded/installed in the camera unit itself 200. In this case the personal computer might not be used at all, or may be used just for transferring the results thereto and displaying the same thereon.

FIGS. 3A and 3B illustrate a hand held electronic device 10 in the form of a smartphone, including a built-in camera unit 200 and flash light source 220, e.g. LED or Xenon light source, and is installed with a processor utility of the present invention (not shown), as well as a memory utility and input/output interface (e.g. a touch screen) 155 typically included in smartphone devices. Also, the phone device may be configured for wireless network communication. As shown in FIG. 3B, an image to be processed, a typical portrait image of a subject 300 may be displayed on the screen. The image may be a partial portrait, showing only the right and/or left eyes of the subject. Also, the region of interest (eye features) upon being identified by the processor, might be marked on the displayed image; these may be such eye features as right and left pupils 310 and Purkinje 320 (reflection of flash light) in right and left eyes.

Figure 3C:
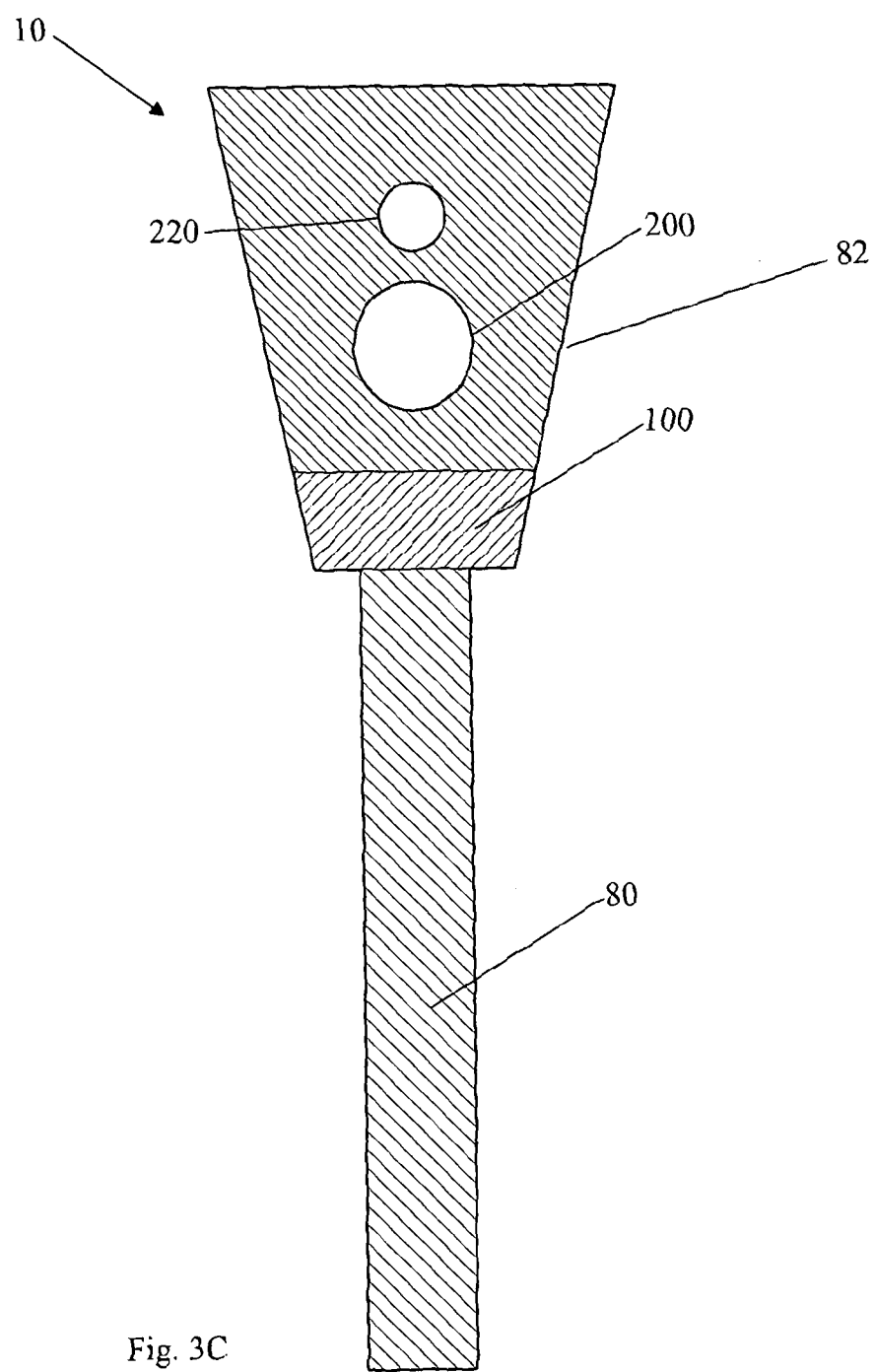
FIG. 3C illustrates how the present invention can be embedded and designed to operate in an ophthalmoscope instrument.

FIG. 3C illustrates an ophthalmoscope device 10 which is configured as an electronic device of the present invention. The ophthalmoscope device 10 typically has a handle portion 80 and an inspection head 82, and further includes a camera unit 200, a flash light source 220 and a processor utility 100 configured as described above. The camera unit 200 and light source 220 are located in the inspection head 82 portion, while the processor may be located in either one of portions 80 and 82 or its modules can be distributed between both portions. It should be noted although not specifically shown that a display may also be provided at either one of portions 80 and 82, also appropriate data communication utilities may be used for communication with external device(s) for accessing reference data and/or transferring the results.

Thus, the device of the invention (i.e. the processor utility and possibly its associated memory with predetermined reference data stored therein) may be embedded in a hand-held (or portable) computing device in the form of a computer software application, e.g. a smartphone application. The processor utility may be configured such that upon being activated by user, provides instructions to the user to capture an image of the subject's face utilizing flash light, and upon detecting that the image does not contain a region of interest, requests the user to take another image until a proper image is provided, and then processes respective image data and outputs the results. The processor utility may be configured to determine whether the image contains a region of interest on-the-fly. That is, the processor utility may be configured to determine whether the image currently shown in a viewfinder image would represent a proper image or not, before the user presses the shutter to take the image. Typically, the viewfinder image is displayed to a user in digital cameras and the user may position the camera until the processing utility determines that the viewfinder image is a proper image and indicates this to the user. The user may then capture the image or the image may be captured automatically by the device at that point.

Figure 4:
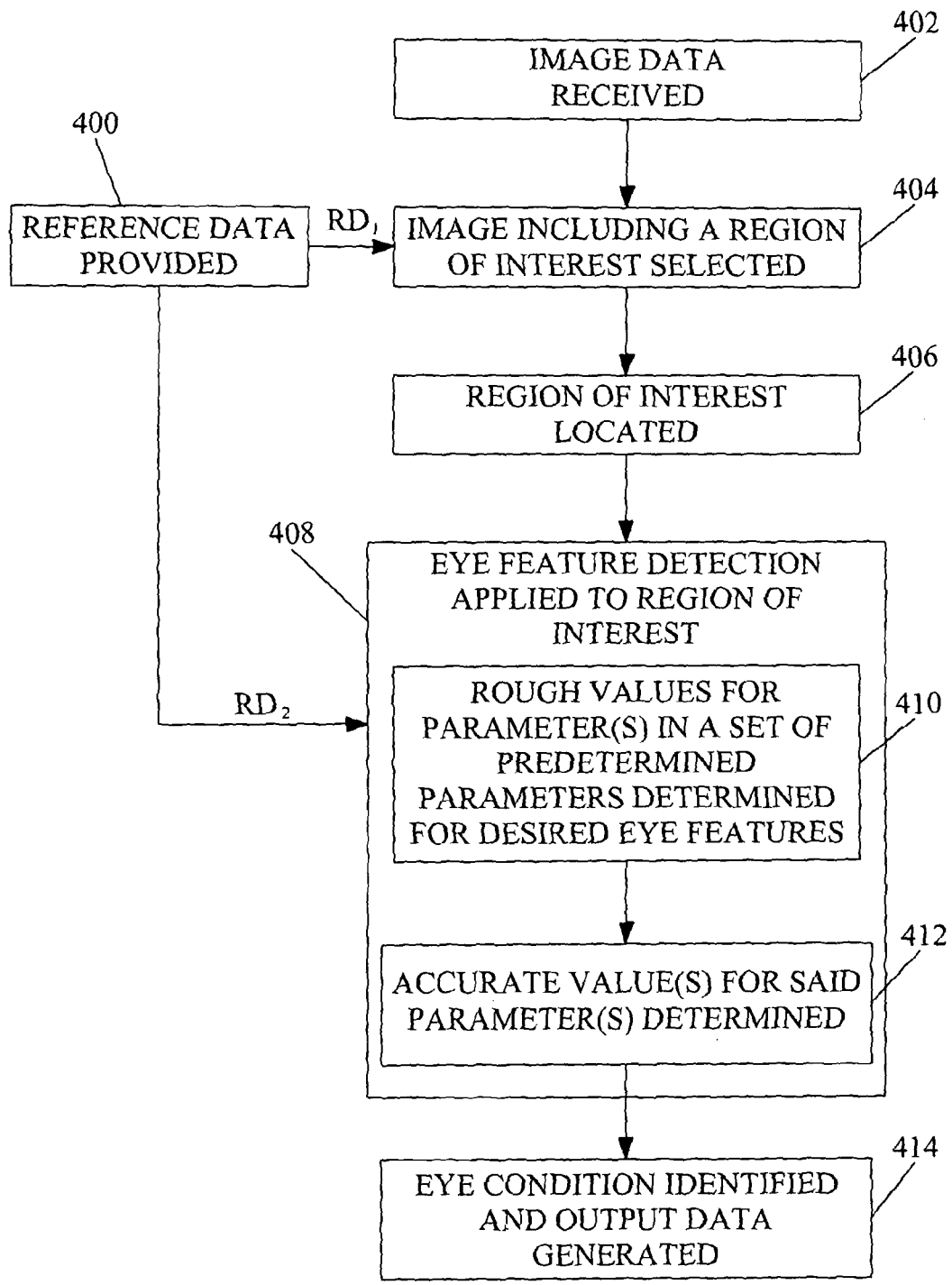
FIG. 4 exemplifies a method of the present invention for detection of abnormal eye conditions.

Reference is made to FIG. 4 illustrating an example of the method of the present invention carried out by the processor utility (100 in FIG. 1).

Initially, certain reference data (or look-up table) is provided (step 400) including first reference data $RD_1$ indicative of pixel values (intensities/colors) associated with different features within a subject's face, and second reference data $RD_2$ indicative of pixel values (intensities/colors) associated with different features within a subject's eye region. For example, the reference data may include ranges for primary colors' values (RGB values) typical for various skin types (colors), RGB ranges typical for sclera pixels, color ranges typical for pupil zone related pixels, etc. It should be understood that the reference data is that previously created based on various test images and once being created is stored for use in actual tests.

An input image data is received by the processor utility (step 402), and the processor utility operates its module 110 to perform a pre-processing procedure (step 404) to select in the image data an image comprising a region of interest including predetermined eye features of at least one of two eyes of the subject, i.e. to identify whether this image data includes an image properly presenting at least one of the left eye (LE) and right eye (RE) regions, or for most applications an image properly presenting those of both the left and right eye regions. In this context, the following should be noted: as will be described further below, most applications require analysis of the two eyes of the subject presented in the same image but there are some applications where analyzing an image of one selected eye region separately is sufficient. In the example below, we refer to the proper image of the subject as that including proper presentation of both the left and right eye regions, but it should be understood that the invention is not limited to this specific example and that the general principles of the invention can be effectively used for medical applications where only one eye is to be properly imaged, as well as various other abnormalities.

The input image data may include a single image, in which case the pre-processor module analyses this image and in case it does not include a region of interest (the proper LE and RE regions), it generates request data (to the user, imager or storage device) for another image. Alternatively, the image data may include multiple images, in which case the pre-processor module analyzes these images and selects the "correct" image for further processing. As indicated above, in some embodiments (for some medical applications, e.g. strabismus detection) the proper LE and RE regions are those where each includes a pupil zone and a Purkinje image.

The pre-processing procedure is aimed at locating the region of interest (the proper LE and RE regions) and generating data indicative thereof (step 406), e.g. by marking those regions in the image or generating a separate image of a part of the face including only these regions. To this end, according to the invention, the pre-processor module utilizes corresponding reference data (first reference data $RD_2$) for obtaining rough data for the location of the LE and RE regions, by classifying pixels in the image according to the first reference data (face-related features) and grouping pixels of different categories relating to the region of interest. This will be described more specifically further below.

An image processing procedure, aimed at detection of eye features required for the specific eye condition identification, is then applied to the selected (roughly located) region of interest in the selected image (step 408). It should be understood that in case this test results in the detection of the existence of all the required eye features in the image it may proceed to the identification of the eye condition.

This image processing procedure 408 has two stages: The first stage (step 410) utilizes corresponding reference data (second reference data $RD_2$) for obtaining rough values of the parameter(s) in the set of predetermined parameters for the desired eye features (e.g. pupil and/or Purkinje image for each of the LE and RE regions), by performing pixel classification and counting as will be described more specifically further below. Considering the detection of strabismus condition, these parameters may include a rough center and a rough size of the pupil. In case that the first stage of image processing results in the detection of these eye features, the process proceeds to the second stage, and if not the image has to be replaced by another one. The second stage (step 412) of the image processing procedure is aimed at determining accurate value(s) for said parameters(s), e.g. center and radius of the Purkinje image. It should be noted that in some embodiments, the system can utilize the rough data for one or more parameters in the set of predetermined parameters in order to detect some eye conditions.

It should be noted that the Purkinje image, being a reflection of a light source (typically flash light), is relatively bright and can be used as a reference point within the eye indicating a general direction from the camera unit (or adjacent to the camera unit) to the subject's eyes. The location of the pupil with respect to the Purkinje image indicates a direction to which the respective eye of a subject is looking (line of sight), and difference of this feature between the two eyes may indicate strabismus condition of the eyes.

In order to determine the accurate value(s) for the eye feature(s), the processor utility (eye feature detection module) operates for re-classifying the pixels within the eye region and processing and analyzing this data. More specifically, in a non-limiting example of the invention, relative brightness of the pixels is used to determine accurate parameter values for the center and radius of the Purkinje image, then this image data is processed to "remove" the Purkinje image from the image (replacing the Purkinje image pixels by other pixels). This procedure will be described more specifically further below. The exact data about the so-obtained parameter(s) of the eye features (e.g. center, size of pupil, average color of pupil) is used to determine the eye condition (e.g. strabismus)—step 414.

Thus, turning back to FIG. 1, the pre-processor module 110 is configured and operable to process input image data 240 to select the proper image as that including an image of a region of interest (which includes desired eye features) and locate said region of interest, while the eye feature detection module 120 is configured and operable to identify and locate the appropriate eye features within the region of interest. The desired eye features include at least one of the pupil and Purkinje image in at least one of left and right eye regions. The set of predetermined parameters for eye features to be detected is defined by the specific application. For example, geometrical and/or positioning parameters of the pupil and Purkinje image may be used for detection of strabismus, the Purkinje image related parameters may be used for detection of anisometropia condition, and the pupil related parameters may be used for detection of retinoblastoma and cataract conditions. The eye condition identifier 130 analyzes data indicative of at least some the detected set of predetermined parameters of the desired eye features and generates data indicative of abnormal conditions, if any.

As indicated above, in some embodiments of the invention, the eye feature detection operates to locate the center of the Purkinje image and the center of the pupil for each eye. In some embodiments, the eye feature detection module may determine also radii of the pupil and Purkinje image. The determined parameters, in the format of pixel units, are received and processed by the eye condition identifier module 130. This module is configured and operable to determine a relation between the eye feature parameters and analyze this relation based on a certain predetermined model. For example, the eye feature parameter(s) of the left eye region is/are compared to similar feature parameter(s) of the right eye region. For example, such a relation between the eye feature parameters may be a degree of symmetry of eye features between the right and left eyes of the subject. Absence of symmetry between the eyes might be indicative of the existence of various abnormal eye conditions. The symmetry condition may be determined by analyzing the pupil location with respect to the Purkinje image for the right and left eyes. Also, for some applications, additional symmetry-related parameters between the eyes are determined, such as physical dimension of the pupils, physical dimension of the Purkinje images in the left and right eyes, and color of either the pupil or the Purkinje image.

Generally speaking, the set of predetermined parameters that can be determined by the technique of the present invention include one or more of the following: center of the Purkinje image for one or both eyes, center of the pupil for one or both eyes, dimension (radius) of the Purkinje image in one or both eye regions, dimension (radius) of the pupil in one or both eye regions, average RGB value of pixels associated with the Purkinje image in one or both eye regions, average RGB value of pixels associated with the pupil in one or both eye regions. One or more of these parameters, e.g. radius of the pupil for each eye, is/are then used by the eye condition identifier for determining a relation between the eye features in the left- and/or right-eye regions and identifying abnormal eye condition(s) in the subject's eyes. For the symmetry condition determination, a relation (difference) between the distance from the centers of the right pupil to the right Purkinje image and the distance between the centers of the left pupil and the left Purkinje image may be determined. This relation is preferably calculated as a vector difference, i.e. calculated along the horizontal and vertical axes separately.

The following are some examples of how the data indicative of the eye features of a subject can be treated for identifying various abnormalities in the eye condition.

For example, the strabismus condition can be detected by determining a relation (difference) between relative positions of the center of the Purkinje image and the center of the pupil in the right eye to those of the left eye, and identifying whether this relation significantly deviates (is above a predetermined threshold) from perfect symmetry condition, which deviation is considered to be abnormal. More specifically, a difference between these positions in the left- and right-eye regions is determined and a relation between this difference and a distance D between the centers of the left- and right-eye pupils (which is calculated in pixel units) is considered. Typically, if such difference exceeds D/200, the deviation is considered significant, and this is assumed to be indicative of strabismus.

Alternatively or additionally, eye features for the left eye region and/or for the right eye region can be analyzed separately (independently) in order to determine strabismus condition for the respective eye. More specifically, an absolute value of a distance between the center of the pupil and the center of the Purkinje image is calculated for the left- or right-eye region along the X-axis (i.e. an axis defined by a line between the centers of the left and right pupils) and/or along the Y-axis. If such distance does not satisfy a predetermined condition with respect to the distance D between the centers of the left- and right-eye pupils, this is considered to be indicative of strabismus of the respective eye. The predetermined condition defines a relation between the distance between the pupil and Purkinje image centers, measured along either the X or Y axis, and the absolute value of the distance D between the centers of the left- and right-eye pupils. Considering the X-axis distance calculation, if the distance between the center of the pupil and the center of the Purkinje image in the eye region exceeds D/80, or considering the Y-axis calculation, if the distance between the center of the pupil and the center of the Purkinje image in the eye region is exceeds D/200, then respective eye is assumed to have strabismus.

Anisometropia condition can be detected by determining such eye features as the radii $R_l$ and $R_r$ of the Purkinje image of the left- and right-eye regions. If a relation between these radii $R_l$ and $R_r$ values does not satisfy a predetermined condition, e.g. $R_l > 1.25 R_r$ or $R_r > 1.25 R_l$, it is considered to correspond to anisometropia condition. Alternatively or additionally, anisometropia condition can be identified by determining and analyzing such eye features as average RGB values of the bright pixels in the Purkinje image of the left eye and of the right eye respectively. It should be noted that typical RGB color scale utilizes 8 bit for each of the Red (R), Green (G) and Blue (B) colors, i.e. a scale of 0 to 255 for each color. If a relation between these values between different eyes does not satisfy a predetermined condition, anisometropia is assumed to exist. A typical relation indicative of such type of abnormality is where one of the average values (between those for the left and right eyes) for R color is brighter than the other by at least 10, and/or one of the average values for G color is brighter than the other by at least 8, and/or one of the average values for B color is brighter than the other by at least 8. If one of the average R, G and B values for one eye is brighter than the corresponding value for the other eye by at least 18, then this might be indicative of anisometropia and also other, more unusual, eye pathologies. It should be understood that the technique of the present invention is not limited to RGB color scale or any specific color scale, and that the colors and the scale thresholds may vary in accordance with the specific application and the model used in the image data processing.

As for the radii of the pupils in the left and right eye regions, a relation between these eye features may be indicative of such an abnormality as anisocoria. More specifically, if the pupil radii values for the left and right eyes are significantly different, e.g. one is larger than the other by a factor of more than 1.4, this is deemed to be abnormal and corresponding to anisocoria condition.

Thus, if any one or more of the above conditions is identified, the system outputs a corresponding result and possibly also recommends conducting further testing by a qualified practitioner. Otherwise, the system outputs a result that indicates the eyes are normal and no further testing is needed. Therefore, the system may output a Pass/Fail result with comments regarding a potential eye condition, if such a condition is detected.

Figure 5A:
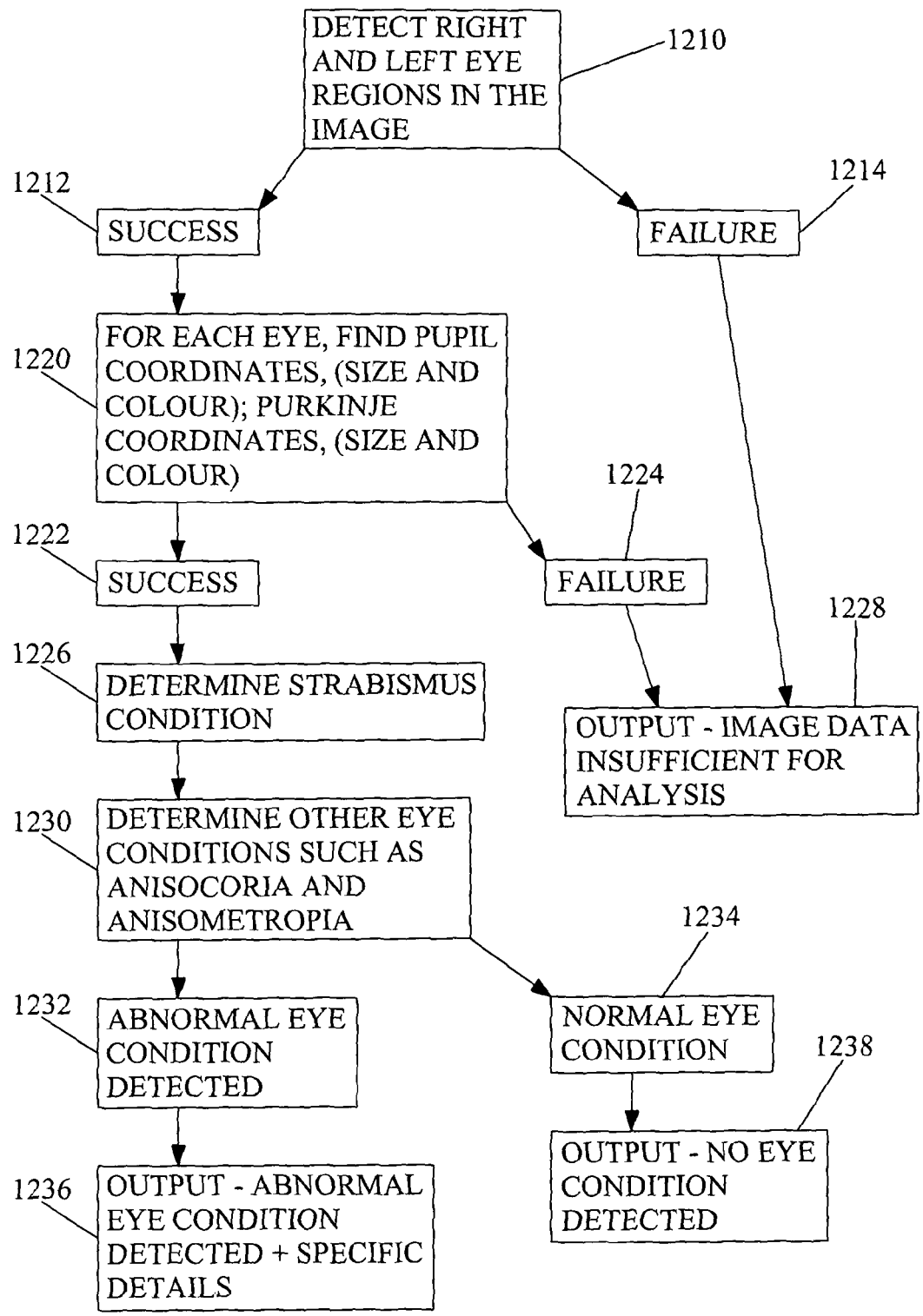
FIGS. 5A to 5F shows a more specific example of the image processing technique according to the invention, where
Figure 5B:
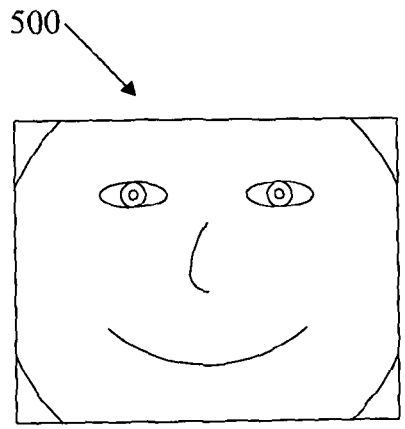

Reference is made to FIGS. 5A to 5F showing a more specific but not limiting example of the technique of the present invention. FIG. 5A shows a flow diagram of the process carried out by a device similar to that illustrated in FIG. 1 for detecting various abnormalities of the subject's eye(s). It should be noted again that a camera unit or a storage device (generally, an imager), as well as a memory utility, may or may not be integral with the device 10. FIGS. 5B to 5F schematically illustrate the eye features identified during successive stages of the processing technique. It should be noted that in the example of FIGS. 5A to 5F, the concurrent and comparative analysis of both the left and right eye regions in the image is utilized, while as described above this is not always necessary.

The processor utility receives image data (e.g. a single image, denoted 500 in FIG. 5B) and performs the pre-processing procedure utilizing the face feature related reference data to identify proper presentation of the right and left eye regions in the image (step 1210). If both eye regions are detected successfully (step 1212), the processing procedure continues towards the image processing of these regions based on eye feature related reference data. However, if no proper image of the right and/or left eye regions is detected (step 1214), the pre-processor utility generates a corresponding notification message (step 1228), and repeats steps 1210, 1212, 1214 with respect to successive images until the proper eye regions are detected in the image.

In the present example, the pre-processing module operates in the following manner for selecting an image including the region of interest (the eye regions). The pre-processing module utilizes reference data relating to such face features as typical pixel colors for various types of skin, RGB ranges typical for sclera pixels, color range typical for pupil pixels, etc. For example, RGB values of around 200, 150, 120 respectively may be typical to face color of fair-skinned people, while RGB values of about 170, 120, 80 are typical for dark-skinned people. Sclera pixels may have RGB values of about 200, 210, 205, while pupil pixels may have RGB values of about 30, 18, 13. Such reference data is obtained from a large database of thousands of photographs taken under certain conditions, e.g. normal photography conditions taken in the "flash" mode, or generally speaking the reference data is based on images taken under conditions similar to those being used in the actual tests. To this end, the pre-processor module may operate to divide the image into two halves around a vertical middle line and process each half separately to detect each of the proper right or left eye regions.

Pixels in the received image are classified, using the above known RGB values as obtained from the reference data, into groups of pixels representing various face features such as "skin pixels" (category A), "sclera pixels" (category B), "pupil pixels" (category C) and "others" (category D). This classification is rough: for example, the pixels of a wet part of the skin may be wrongly classified as sclera-related ones because such skin is shiny.

This rough classification is used as a test for whether the image is acceptable for further processing. If, in either half of the image, the number of skin-related pixels falls below a predetermined threshold (typically ⅓ of the number of pixels in the image half), or the number of sclera-related pixels falls above or below a certain threshold (typically 1/500 and 1/10000 of the number of pixels in the image half respectively), or the number of pupil-related pixels falls above or below a corresponding threshold (typically 1/100 and 1/10000 of the number of pixels in the image half respectively), then the image is deemed unacceptable. Accordingly, a corresponding notification is generated (e.g. displayed to the operator) instructing either the operator or the program to shift to another image or obtain another image from the imager.

The pixel classification may be verified based on relative location of the pixels of different classes. More specifically, pixels classified as pupil-related and possibly also iris-related, should be in the vicinity of the pixels classified as sclera.

Figure 5C:
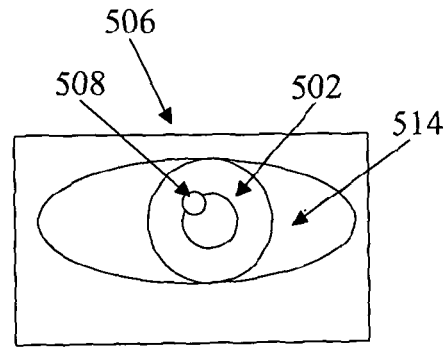
Figure 5D:
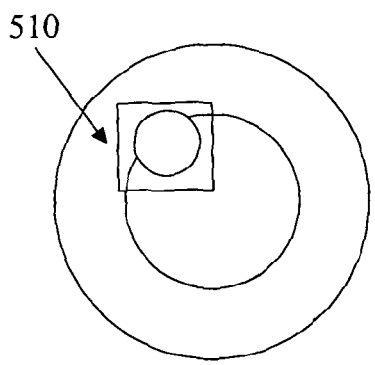
Figure 5E:
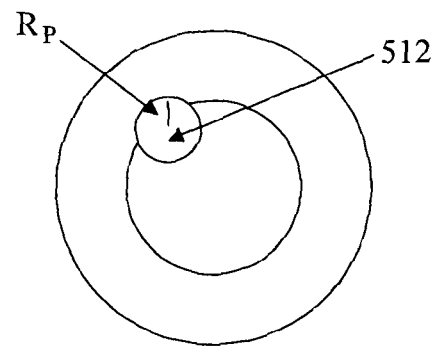
Figure 5F:
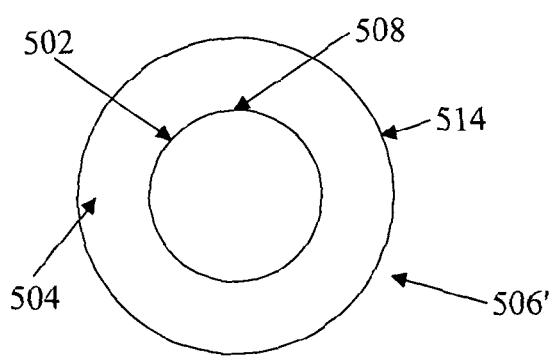

A rough location of the region of interest (eye region) is determined, by grouping and counting of all adjacent pixels associated with different parts/features of the eye region, i.e. pupil and sclera zones denoted 502 and 504 in FIG. 5C, to a group containing N pixels. A weighted center of this group of pixels is calculated and a rectangle 506 is drawn around the so-obtained center, where the rectangle has a width four times larger than its height and covers an area being four times the number of pixels N.

Preferably, the pixels are re-classified within the rectangle 506 using the above-described classification technique based on the RGB values for pixels of different features in the eye region. More specifically, in each eye region a count is performed of the pixels by their RGB values considering that in a typical eye region there are pixels related to sclera of RGB values of about 200, 200, 200, pixels related to eyelashes or pupil of RGB values of about 30, 15, 15. It should be understood that these values, and similar values mentioned below, are not limiting examples of the reference data.

Also, for the purposes of the present invention or at least some embodiments thereof, the eye region to be selected as successful/proper (step 1212) includes a Purkinje image 508. For this purpose, the brightest pixels are identified within each rectangle (eye region), with limited tolerance to color variations (e.g. pixels around RGB values of 254, 252, 250 with tolerance of ±4), as defining the Purkinje image, i.e. flash reflection.

As indicated above, upon identifying and locating the proper eye regions, the processor utility proceeds to the actual image processing based on the eye feature related reference data to determine one or more parameters of the set of predetermined parameters of the eye feature(s)—step 1220. Considering the embodiment requiring Purkinje image detection, the processor utility operates to count a number M of selected (brightest) pixels related to the Purkinje image 508, and calculates a weighted center of the Purkinje image to be considered a rough center of the Purkinje image. Then, a rough radius of the Purkinje image (being large enough to cover the Purkinje image) is determined as a square root of the number of the Purkinje image pixels M, and a bounding square region 510 is defined having sides twice the size of the radius.

These rough values of the center and radius parameters of the Purkinje image are used to arrive at more accurate values, as follows: Within the square 510, pixels are re-classified according to the corresponding reference data about typical values of Purkinje image pixels (category PA), Purkinje boundary pixels (category PB, typically having values intermediate between very bright and very dark), and other pixels (category PC). A more precise weighted Purkinje image center 512 is calculated using the brightness of the Purkinje boundary pixels as their weight. When calculating the weighted center, a bright pixel (category PA) counts as one pixel; an intermediate pixel (category PB) counts as less than one pixel, in proportion to how bright it is. Thus, a pixel that's halfway between fully bright and fully dark will be counted as half a pixel. The newly calculated center in pixel units may or may not be an integer. Similarly, the classification of the Purkinje image pixels according to the brightness (in proportion to full brightness) is used to determine an accurate radius of the Purkinje image. This radius $R_p$, is determined as the square root of the number of Purkinje image pixels divided by $\pi$; the radius of the Purkinje image in pixel unit may be a non integer value.

Then, the center of the pupil zone of each eye is located in the rectangle region 506. To this end, the Purkinje image is removed from the rectangle 506. The processor may thus operate to make a copy of the rectangle region 506 and treat that image to remove the Purkinje zone therefrom and replace the respective pixels by those related to the pupil. The pixels associated with the area covered by the Purkinje image are now assigned with RGB values being a weighted average of other eye-part pixels nearby: each of the "erased" pixels is assigned with the RGB value of the nearest pixel outside the Purkinje image, resulting in a rough replacement of the Purkinje image by the pupil and iris zones 502 and 514. The pixels within such eye region 506' (i.e. with the removed Purkinje zone 508) are re-classified as corresponding to pupil 502, iris 514, sclera 504 and other (including skin, eye lashes, etc.) as indicated above utilizing the corresponding reference data.

More specifically, dark pixels in the eye region are classified as pupil-related pixels, with a tolerance of ±8 in each of the RGB values around RGB values of about 12, 12, 12, and a number K of these pixels is determined. Then, a weighted center of these dark pixels is determined and considered as a rough center of the pupil, and a rough radius of the pupil, being large enough to cover the pupil zone, is determined as a square root of the number of pupil associated pixels K, and a square having a side of twice the radius is used in further analysis. The latter is aimed at determining accurate values for the pupil center and radius, and includes the pixel reclassification and counting. This reclassification includes the pixel division into "pupil pixels" (typically very dark), "pupil border pixels" (typically having slightly brighter values) and "other pixels". A weighted center is calculated using this classification where the pupil border pixels are given a weight proportional to their darkness. The result is considered as an accurate center of the pupil in each eye (which may or may not be an integer in the pixel units). An accurate radius of the pupil is calculated based on the pupil pixels and pupil border pixels classification. The radius of the pupil is calculated as a square root of the number of the pupil pixels divided by $\pi$. Similarly, the radius value in pixel units may not be integer.

As indicated above, if during the eye feature detection stage 1220 one or more of the required features cannot be properly determined (step 1224), an appropriate notification is generated (step 1228) requesting another image data, and the eye feature detection stage is repeated upon successful determination of all the required features (step 1222). It should be noted that the processor utility may be configured to stop the entire procedure upon detecting that a number of faults in the feature detection procedure reaches a predetermined threshold. In this case, the system generates a failure notification to the operator which states that analysis cannot be performed on the image data supplied to the system.

Data indicative of the detected eye features is processed by the eye condition identifier module to determine the existence and possibly also a degree of one or more abnormalities, e.g. strabismus condition of the eyes (step 1226). As described above with reference to FIG. 4, this procedure includes determination of one or more relation(s) between the calculated eye feature parameters, and/or a relation between the eye feature parameters and the distance between the left- and right-eye pupils, etc. According to some embodiments, more than one abnormality can be detected than those described above (step 1230). The eye condition identifier module may identify that the eye features correspond to a normal eye condition (step 1234), and generate an appropriate notification (step 1238). If any abnormal eye condition is detected (step 1232), the system generates corresponding notification which preferably includes specific details related to the eye condition found (step 1236).

The methods and apparatuses disclosed herein deal primarily with digital photographs of a subject, normally including one or both eyes and a significant part of the face. It is desirable for these digital photographs to provide a clear view of most of the one or both eyes, as well as of the reflection of a light—usually the camera flash—in each eye (a Purkinje image). The analyses performed by the methods and apparatuses disclosed herein are made easier if the digital photographs are in focus and well lit.

For most users, it is not difficult to take a photograph with a digital camera as it relies on very basic photographic skills, which most adults possess. However, verification that the photo meets all the criteria to facilitate easy processing in the methods and apparatuses disclosed herein is not easily determined by a user. Moreover, such criteria are not easily determined quickly by a user. This is especially the case when the subject is a child or infant and it is, therefore, important to validate the photograph quickly to determine whether additional photographs are required, before the child or infant loses patience with the process.

Returning again to the preprocessing procedure described above, validation of an image can be used to give a user quick feedback on a photograph that has just been taken. This allows the user to know almost instantly whether a captured image is suitable for analysis and, if not, to capture an alternative image after being requested to do so. This reduces the number of images that a user may need to capture as, in known systems a user has no indication of whether an image is suitable or not and so, to be confident, the user will take a high number of images in the hope that one is suitable. Even then, it is not necessarily the case that, of the high number of images, one image has been captured that satisfies the criteria, which will result in an invalid test and require an alternative image to be captured at some time later.

In addition, validation may be used to give a user feedback on a viewfinder image before an image is captured by the user. If the photograph, or the viewfinder image, passes validation, it may be determined to be good for analysis as described above. Otherwise, the user may be presented with feedback to explain that another photograph is needed, or that the viewfinder image is not acceptable for image processing, and why.

If the preprocessing concerns a captured photograph, the feedback may comprise a pop-up box displayed on a screen of the device, instructing the user to capture an alternative image. If the preprocessing concerns a viewfinder image, the feedback may comprise an indication that the current viewfinder image is not suitable. The indication may change when the viewfinder image is suitable to instruct the user to capture the image. The indication may, for example, be a red light when the viewfinder image is not suitable, and a green light when the viewfinder image is suitable.

Thus, the validation process is configured to output a code which indicates either a "success", i.e. the captured photograph or viewfinder image is suitable for analysis, or a "failure", which may be one or more of:

"Failure—no two eyes". This output is produced by the methods and apparatuses disclosed herein if two eyes are required for later analysis, and the preprocessing procedure determines that two eyes are not present. This output may be presented to the user by a message explaining that two eyes are not seen in the photograph.

"Failure—out of focus". This output is produced by the methods and apparatuses disclosed herein if the preprocessing procedure determines that the focus of the captured photograph or viewfinder image is below a threshold value required for later analysis of the image. This output may be presented to the user by a message explaining that they should make sure the next photograph is in focus.

"Failure—face too small". This output is produced by the methods and apparatuses disclosed herein if the preprocessing procedure determines that the size of the face of the subject is below a threshold value required for later analysis of the image. This output may be presented to the user by a message instructing them to move the camera unit closer to the subject, or to zoom in further.

"Failure—face tilted". This output is produced by the methods and apparatuses disclosed herein if the preprocessing procedure determines that the face of the subject is not looking directly into the camera unit, but is angled away from the camera unit. This output may be presented to the user by a message explaining that the subject's face should be straight, not titled, in the next photograph or viewfinder image.

Validation may be performed using the following decision making process, which is exemplary and shows the process for analysis requiring two eyes:

If no eyes are found during validation, the analysis stops and the validation process outputs a "Failure—no two eyes" code.

If only one eye is found during validation, the analysis stops and the validation process outputs a "Failure—no two eyes" code.

If more than two eyes are found during validation, the analysis stops and the validation process outputs a "Failure—no two eyes" code. This can happen, for example, if two people are in the photo with their faces close together.

If, during validation, the eyes found are smaller than a pre-determined minimum threshold size, the analysis stops and the validation process outputs a "Failure—face too small" code. This can happen, for example, if the camera unit is too far away from the subject.

If, during validation, the eyes found to have a difference in relative vertical placement greater than a threshold value, the analysis is stopped and the validation process outputs a "Failure—face tilted" code. The difference in relative vertical placement may be determined by an angle of a line taken between the eyes to a horizontal axis of the image. The threshold value may be, for example, in the range from 20 degrees to 40 degrees. In a specific example, the threshold may be 30 degrees. This can happen, for example, if the subject's face is held diagonally, or if the user fails to hold the camera sufficiently straight when taking the photograph.

If, during validation, the size of a light reflection in either eye is larger than a pre-determined threshold maximum size, the analysis is stopped and the validation process outputs a "Failure—out of focus" code. If a distance between the pupils of the eyes is given by d, the threshold maximum size may, for example, be in the range from d/75 to d/85. In one specific example, the threshold maximum size may be d/80. This is because, typically, when the photo is somewhat out of focus, the reflection turns from a small clear circle into a much larger, blurred, patch.

If validation fails at any other stage, the analysis is stopped and the validation process outputs a "Failure—no two eyes" code.

It is possible, that a normal subject, i.e. a subject with no eye abnormalities, may appear strabismic in some photographs. This may be because the analysis of an image of a subject described above is based on symmetry, and symmetry relies on the subject looking straight ahead and trying to focus on the camera. If the subject's gaze wanders before an image is captured, the subject may then appear strabismic even when they are not.

To overcome this, the analysis may be expanded such that only a single "pass" indication for one image is required to pass a subject, e.g. to determine that a subject is not strabismic, but a plurality of "fail" indications are required for separate images for the apparatus to return a "fail" for a subject, e.g. to determine that a subject is strabismic. This may be implemented as in the exemplary method provided below.

If analysis by the eye condition identifier module determines that an image (or photograph) is indicative of normal eyes (e.g. not exhibiting strabismus), the image is passed and so to is the subject. An output to the user instructs them that no further action is needed.

Otherwise, the system increments a count corresponding to a number of fails against a particular subject. In the case of determining whether a subject has strabismus, the count represents the number of "strabismic-looking" images for a subject. As long as this count is below a threshold number, the apparatus is configured to indicate to the user that another image should be captured. The threshold may be in the range from two to five and, in a specific example, may be three.

The apparatus is configured to pass a subject at any time when analysis determines any image to be passed.

The apparatus is configured to fail a subject if the fail count for a subject reaches the threshold.

Thus, a subject may be deemed to be normal with one photo only, but a strabismic subject—which is typically a small minority of subjects—will have to have three images captured before the apparatus reliably determines that the subject may require further testing.

Thus, the present invention provides a novel technique for fully automatic, simple and effective detection of various abnormalities in the subject's eye condition, e.g. strabismus. The present invention may be utilized as a computer embedded software, operating on any computing system/electronic device being connectable to receive image data or integral with a camera unit for generating image data. Such a computing system or electronic device may be a personal computer, laptop, or any other hand held computing device such as smartphone, tablet, PDA, etc.). Those skilled in the art will readily appreciate that various modifications and changes can be applied to the embodiments of the present invention as hereinbefore described without departing from its scope defined in and by the appended claims.

The invention claimed is:

1. An electronic device comprising a processor utility configured and operable for processing image data, determining whether an abnormality exists in an image of a subject's eye, and generating corresponding output data, said processor utility comprising:
   a first processor configured and operable for selecting in the image data an image comprising a region of interest including predetermined eye features of at least one of two eyes of the subject, the first processor further configured and operable for pre-processing the image to determine whether it is suitable for image processing and for providing an indication of the determined suitability of the image;
   an eye feature detection utility configured and operable for applying an image processing algorithm to a suitable image for determining one or more parameters of the eye features from a set of predetermined parameters, wherein determining one or more parameters of the eye features comprises determining a number of pupil pixels in a suitable image; and
   an eye condition identifier utility configured and operable for processing and analyzing said one or more parameters and generating data indicative of whether an abnormality exists in the image.

2. The device of claim 1, further comprising a camera assembly for capturing the image data.

3. The device of claim 1, wherein the processor utility is configured to determine whether the image comprises two eyes, and provide a negative indication if the image comprises fewer than two eyes.

4. The device of claim 1, wherein the processor utility is configured to determine whether the image comprises eyes of a subject and the size of the eyes in the image, and provide a negative indication if the eyes in the image have a size smaller than a predetermined threshold value.

5. The device of claim 1, wherein the processor utility is configured to determine the relative vertical placement of a first eye and a second eye within the image, and provide a negative indication if the difference in relative vertical placement of the first and second eyes is greater than a predetermined threshold.

6. The device of claim 1, wherein the eye condition identifier module is configured to pass the image if no data indicative of an abnormality exists in the image, and to fail the image if data indicative of an abnormality exists in the image.

7. The device of claim 6, wherein the eye condition identifier module is configured to generate data indicating that a subject's eye comprises abnormalities if the number of failed images for a subject is greater than or equal to a pre-determined threshold.

8. The device of claim 1, wherein the image comprises a captured image, and wherein, if the image is not suitable, the processor utility is configured to generate a request to a user that an alternative image be captured.

9. The device of claim 1, wherein said region of interest comprises a Purkinje image.

10. The device of claim 9, wherein said first processor module is configured and operable for carrying out said selection by processing an image using first reference data indicative of pixel values corresponding to face features to obtain rough data about the region of interest in said image based on classifying pixels in the image according to said first reference data and grouping pixels of different categories relating to the region of interest.

11. The device of claim 9, wherein said eye feature detection module is configured and operable for processing the region of interest using second reference data indicative of pixel values relating to eye features to obtain a rough value of said one or more parameters of the eye features by classifying pixels in the region of interest according to said second reference data and counting pixels relating to at least one eye feature.

12. The device of claim 11, wherein said eye feature detection module is configured and operable for using the rough values of said one or more parameters for the eye feature and re-classifying the pixels related to said at least one eye feature, and weighting values of said re-classified pixels.

13. The device of claim 1, wherein said eye condition identifier module is configured and operable to determine a relation between relative positions of a center of a Purkinje image and a center of a pupil zone in the right eye to those of the left eye, and identifying a deviation of said relation from a predetermined value being indicative a degree of asymmetry corresponding to strabismus condition.

14. The device of claim 13, wherein said eye condition identifier module is configured and operable to determine said relation in a form of a vector distance between a center of a pupil and a center of a Purkinje image in at least one of the left and right eye regions in the image, and to identify a deviation of said relation from a predetermined value being indicative of strabismus condition of said at least one eye.

15. The device of claim 1, wherein said processing of the image data comprises:
(a) locating right and left eye regions in the selected image;
(b) locating zones corresponding to pupils of the right and left eye regions;
(c) locating a zone in the eye region corresponding to a Purkinje image, for right and left eyes of the subject;
(d) determining a relative location of the Purkinje image with respect to the pupil zone, for the right and left eye regions; and
(e) analyzing said relative location, and generating data of whether an abnormality indicative of a strabismus condition of the subject exists in the image.

16. The device of claim 1, comprising a light source for illuminating the surroundings at least during a time of image acquisition by a frame grabber.

17. The device of claim 1, being configured as one of the following: a camera unit, a phone device, a portable computer, tablet, PDA, an ophthalmoscope tool.

18. The method for determining whether an abnormality exists in an image of an eye of a subject using an electronic device comprising a processor utility configured and operable for processing image data, determining whether an abnormality exists in an image of a subject's eye, and generating corresponding output data, the method comprising:
receiving image data at said processor utility, the image data being indicative of one or more images,
processing said image data, by the processor utility, for selecting in the image data an image comprising a region of interest including predetermined eye features of at least one of two eyes of the subject,
for pre-processing the image to determine whether it is suitable for image processing and
for providing an indication of the determined suitability of the image;
if the image is suitable, applying, by an eye feature detection utility, an image processing algorithm to the image for determining one or more parameters of the eye features from a set of predetermined parameters, wherein determining one or more parameters of the eye features comprises determining a number of pupil pixels in a suitable image;
processing and analyzing, by an eye condition identifier utility, said one or more parameters, and generating data indicative of existence or absence of one or more abnormalities in the image data.

19. A computer program product embedded on a non-transitory computer-accessible medium and comprising a computer readable program code configured and operable for executing the method for determining whether an abnormality exists in an image of an eye of a subject using an electronic device comprising a processor utility configured and operable for processing image data, determining whether an abnormality exists in an image of a subject's eye, and generating corresponding output data, the method comprising:
receiving image data at said processor utility, the image data being indicative of one or more images,
processing said image data, by the processor utility, for selecting in the image data an image comprising a region of interest including predetermined eye features of at least one of two eyes of the subject,
for pre-processing the image to determine whether it is suitable for image processing and
for providing an indication of the determined suitability of the image;
if the image is suitable, applying, by an eye feature detection utility, an image processing algorithm to the image for determining one or more parameters of the eye features from a set of predetermined parameters, wherein determining one or more parameters of the eye features comprises determining a number of pupil pixels in a suitable image;
processing and analyzing, by an eye condition identifier utility, said one or more parameters, and generating data indicative of existence or absence of one or more abnormalities in the image data.

20. A handheld electronic device comprising a camera for acquiring images of a subject's face and generating image data and a processor utility configured and operable for processing the image data, determining whether an abnormality exists in an image of a subject's eye, and generating corresponding output data, said processor utility comprising:
a first processor configured and operable for selecting in the image data an image comprising a region of interest including predetermined eye features of at least one of two eyes of the subject, said selecting comprising processing an image using a first reference data indicative of pixel values corresponding to face features to obtain rough data about the region of interest in said image based on classifying pixels in the image according to said first reference data and grouping pixels of different categories relating to the region of interest, the first processor being further configured and operable for pre-processing the image to determine whether it is suitable for image processing and for providing an indication of the determined suitability of the image;

an eye feature detection utility configured and operable for applying an image processing algorithm to a suitable image for determining one or more geometrical and positioning parameters of the eye features, wherein determining one or more geometrical and positioning parameters of the eye features comprises determining a number of pupil pixels in a suitable image, said applying of the image processing algorithm comprising using second reference data indicative of pixel values corresponding to eye features to obtain a value of said one or more of geometrical and positioning parameters of the eye features by classifying pixels in the region of interest according to said second reference data and counting pixels relating to at least one eye feature; and an eye condition identifier utility configured and operable for processing and analyzing said one or more geometrical and positioning parameters and generating data indicative of whether an abnormality exists in the image.

\* \* \* \* \*